United States Patent [19]

Bernstein

[11] Patent Number: 5,716,976
[45] Date of Patent: Feb. 10, 1998

[54] METHOD OF TREATMENT FOR CARBOHYDRATE ADDICTION

[76] Inventor: Richard K. Bernstein, 1160 Greacen Point Rd., Mamaroneck, N.Y. 10543

[21] Appl. No.: 615,616

[22] Filed: Mar. 13, 1996

[51] Int. Cl.[6] .................................................. A61K 31/415
[52] U.S. Cl. ........................................... 514/386; 514/561
[58] Field of Search ...................................... 514/386, 561

[56] References Cited

PUBLICATIONS

Embase Abstract 90222349 (1990)–Wurtman.

*Primary Examiner*—Zohreh Fay
*Attorney, Agent, or Firm*—Kane, Dalsimer, Sullivan, Kurucz, Levy, Eisele and Richard

[57] ABSTRACT

A method is described for alleviating carbohydrate addiction by administration of anorexients on a schedule that avoids tolerance to the anorexient.

27 Claims, No Drawings

METHOD OF TREATMENT FOR CARBOHYDRATE ADDICTION

BACKGROUND OF THE INVENTION

1. Field of The Invention

The invention relates to the treatment of diet-related diseases in humans and more particularly to a method of alleviating carbohydrate addiction suffered by a human.

2. Brief Description of The Prior Art

It is well known that a number of human diseases are aggravated by the ingestion and assimilation of carbohydrates. For example, type I and type II diabetics suffer long term complications of diabetes as a result of failure to control blood sugar levels. Abnormal blood sugar levels are directly related to excessive ingestion of carbohydrate.

A certain number of individuals, once they have given up bread, sweets, and the like, find their craving for carbohydrates gone. Many Type I diabetics and a small number of Type II's find they can control their blood sugars and, if appropriate, lose weight without relying on anorexient medication. Somehow the craving, if present, just goes away.

However, the larger number of Type II and some Type I diabetics do not find their craving for carbohydrate diminished. They find themselves in distress, just like any addict would, who is denied the target of his addictions. The fact is, many individuals do become addicted to carbohydrate, in the same way one can become addicted to a narcotic, but more commonly by inheriting the "thrifty genotype". The so-called "thrifty genotype" was hypothesized in the mid-1960s as a gene which directs storage of energy by the body when little food is available. Much of available carbohydrate is converted in the body to fat and more carbohydrate is craved. When food availability increases, the gene continues to direct this conversion and craving, with the result that obesity occurs.

In those with the thrifty genotype, it is speculated that a lack of certain neurotransmitters in the apetite centers of the brain leaves the individual with a feeling of hunger and a mild dypsphoria. Eating carbohydrate temporarily causes the individual to feel calm and less hungry, the initiation of addiction to the carbohydrte.

The nature of any addiction has been the subject of much research.

There is a notion gaining recognition within the medical community called the "homeostatic theory of biochemical addiction", which states in essence that the brain attempts to compensate for the prolonged presence of (in the case of carbohydrate addiction and obesity) certain neurotransmitters by diminishing their effects and incorporating them into the ongoing activity of the brain. It is well established that dietary carbohydrate enhances production in the brain of at least one "mood relaxing" neurotransmitter, serotonin. Furthermore, carbohydrate, by increasing blood insulin levels, facilitates entry into the brain of L-tryptophan, an amino acid component of dietary proteins. Once in the brain, it can be converted to the neurotransmitter serotonin.

If you look at some individuals who may currently be slim, and not overweight, but who are eating lots of sweets over a prolonged period of time, in effect, they are bathing their neurons in serotonin. According to the homeostatic theory, their brains may adjust to the enhanced presence of the neurotransmitter by either down-regulating its normal production, or down-regulating the sensitivity or number of its receptors. They may need more and more Carbohydrate to achieve the same effect (the classic "tolerance" effect of addiction). This may be the same reason why exercise addicts run in sub-zero weather, and possibly why workaholics are constantly on the go. Their brains have grown accustomed to certain levels of particular biochemicals, and simply to maintain a normal, placid state, they must feed their addiction, just like a heroin or cocaine addict. When serotonin levels are diminished, a carbohydrate addict will experience renewed craving. Numerous studies have shown that the portions of the brain that are involved with hunger and satiety are also involved with mood. Clinical depression has been linked with these brain centers. Indeed, depression may carry with it changes in eating behavior (such as a reduced or increased appetite). Studies have also shown that by using medications that selectively block serotonin receptors, an enhanced desire for carbohydrate-rich foods occurs. When the same subjects were given fenfluramine (Pondimin), a serotonin agonist (an agonist is a helper, the opposite of an antagonist), this enhanced desire for carbohydrates disappeared. Interestingly, desire for other types of food was not affected.

Research by Richard J. and Judith J. Wurtman of the Department of Brain and Cognitive Science at the Massachusetts Institute of Technology (MIT) showed that "carbohydrate intake is regulated independently of calorie intake," and that the consumption of carbohydrate can significantly improve mood, a result of increased levels of serotonin in the brain. Serotonin levels were enhanced after a carbohydrate-rich, protein-poor meal "due to increased uptake into the brain of serotonin's precursor, the amino acid tryptophan". More recently, additional mechanisms have been proposed that would also facilitate the effect of carbohydrate upon serotonin levels. Importantly, the Wurtmans also discovered that consumption of protein actually prevented serotonin synthesis from tryptophan because blood levels of other "amino acids that normally competed with tryptophan for uptake into the brain were increased following protein consumption."

These findings led the Wurtmans to study patterns of snacking in obese patients. They uncovered information of great relevance to the control of obesity and of diabetic blood sugars. First, they found that patterns of snacking were peculiar to the individuals doing the snacking. While there were common themes, each person had his or her own craving clock. They also observed that when given the choice between carbohydrate and protein-rich snack foods, nearly every snacker chose carbohydrate nearly every time. Most importantly, they found that when treated with Pondimin, a substance that increases brain serotonin levels, "the consumption of carbohydrate-rich snacks decreased significantly." In other words, it is possible to substitute a pill for carbohydrate in order to achieve dietary satisfaction.

SUMMARY OF THE INVENTION

The invention comprises a method of alleviating carbohydrate addiction in a human suffering from said addiction, which comprises;

administering to a human suffering from carbohydrate addiction a first anorexient or combination of anorexients in amounts sufficient to relieve the addiction for a period of time insufficient to develop tolerance to the administration; and then replacing said anorexient or combination of anorexients with appropriate amounts of a different anorexient or combination of anorexients and periodically alternating the two anorexient regimens;

whereby the addiction is alleviated.

The term anorexient refers to prescription or non-prescription medications, amino acids, and herbal preparations that can reduce or eliminate carbohydrate craving. Using my invention, therapy with them will be long-term or even life long for most of those who crave carbohydrate. Anorexients will help to achieve and to maintain an appropriate weight and, for diabetics, their help in controlling addiction to carbohydrate will facilitate maintenance of normal blood sugar levels.

DETAILED DESCRIPTION OF THE PREFERRED EMBODIMENTS OF THE INVENTION

One aspect of using anorexients as a long-term treatment for the chronic condition of carbohydrate addiction is that in virtually all the studies done on these medications, either singly or in combination, patients develop a tolerance to their anorexient effects. As a consequence, their utility usually diminishes over time. This would seem in part to be explained by the homeostatic theory described above. In these studies, most patients lost weight initially, a few kept the weight off with long-term therapy with the same anorexient or combination of anorexients, but most users rapidly regained the lost weight. It is a peculiarity of certain of these drugs that they generally do not (for whatever reason) lose their effectiveness as antidepressant, anti-anxiety, or anti-hypertensive drugs over time.

A way to avoid developing a tolerance to these preparations is to rotate them on a scheduled basis, thus not allowing them to be part of the homeostatic environment of the brain, and never giving the brain a chance to acquire tolerance. Two, and in occasional cases, three or four different anorexient regimens, usually from different categories of anorexient are used during which the administration is rotated on a schedule, for example, a weekly basis.

There are many known anorexients, and they all seem to work in one of four general ways: by stimulating manufacture of specific neurotransmitters, in the pre-synaptic axons of the brain; by stimulating release of specific neurotransmitters into the synapses of the brain; by increasing the affinity of receptors for the neurotransmitters that affect them; or by impeding the pre-synaptic reuptake or destruction of neurotransmitters that have entered synapses.

Neurotransmitters and Receptors

The central nervous system (brain and spinal cord) and peripheral nervous system (outside the brain and spinal cord) are made up of many miles of nerve fibers, which in turn consist of billions of individual nerve cells or neurons. Neurons communicate with one another via chemicals called neurotransmitters. Separating the neurons are synapses, tiny spaces into which neurotransmitters are released. Each neuron is an individual cell body equipped with a long transmitter, or axon, which extends from the cell, and many dendrites, that also extend from the cell body and receive signals from axons of other neurons. The receiving ends of dendrites contain receptors for neurotransmitters emitted by axons. As important as neurotransmitters are, the receptors that collect, process, and send on their signals are at least of equal importance. Neurons are arranged in networks within the brain, responsible for specific groups of functions. Relatively few neurotransmitters can do manifold jobs, depending upon which receptors or circuits they stimulate.

There are more than 100 known neurotransmitters at work in the human brain, and it is likely that there are others that have yet to be discovered. Within these 100 plus neurotransmitters there are four major categories. The most widely distributed in the brain consist of amino acids from our dietary intake of proteins, such as glutamine and glycine. There are also the neuropeptides, made up of short chains of amino acids, which seem to have regulatory effects on the actions of the other neurotransmitters. Less widely distributed are the two subgroups of monoamines, serotonin, which is synthesized from the amino acid tryptophan, and dopamine and norepinephrine, which are derived from the amino acids tyrosine and phenylalanine. Both subgroups of monoamines seem to be concentrated in particular areas of the brainstem but are utilized by neurons whose long axons extend throughout the brain.

These are the neurotransmitters in the brain which most concern our consideration of blood sugar maintenance and weight control. All of the neurotransmitters together provide an astonishing and subtle array of information, but the three monoamines, with the help of their receptors and of the modulating neuropeptides, are the principal players in issues of emotion, pleasure, anxiety, and hunger. The same receptors that receive signals from one of these neurotransmitters are sometimes able to utilize the others. Each neurotransmitter can have different effects when encountering different receptors, allowing for even more subtlety.

The anorexients employed in the method of the invention affect the neurotransmitters and receptors involved in carbohydrate addiction. There are many such anorexients, which can be identified and classified in several groups such as serotonin agonists.

Serotonin Agonists

The serotonin agonists currently make up a major category of anorexients. Much of the research that is being done to date on the correlation between mood and food suggests that serotonin has a great impact on eating behavior.

Serotonin agonists are usually antidepressants such as sertraline (Zoloft) and fluoxetine (Prozac). Most are selective serotonin reuptake inhibitors, or SSRI's, and they operate exactly as you would expect from drugs with such a name. When a neuron "fires" and serotonin is released by an axon, any excess that remains in the synapse is reabsorbed or "reuptaken" by the neuron that secreted it. An SSRI selectively blocks the reabsorption of serotonin so that it remains in the synapse and continues to stimulate the second or post-synaptic neuron.

SSRIs can suppress dopamine activity, so it may be beneficial to combine them with another preparation that has a dopamine agonist effect or to use an SSRI that is also a dopamine agonist.

Another group of serotonin agonists are the precursors of the neurotransmitter (that is, their chemical makeup so closely resembles that of the neurotransmitter that the neuron can synthesize the neurotransmitter from it). Tryptophan, an amino acid, is the body's resident precursor for serotonin. Spiruline, an over-the-counter preparation derived from seaweed, is a rich source of natural tryptophan. Serotonin precursors can be used effectively in combination with SSRIs to increase the effectiveness of both as anorexients.

Dopamine and Norepinephrine Agonists

Pure dopamine agonists such as levo-dopa, pergoglide (Permax), and bromocriptine, are used to treat Parkinson's disease. This is a progressive brain disorder that culminates in a virtually total loss of dopamine production in the nigro-striatial tract and certain other circuits in the brain. It is characterized in its end stage by a rigid, catatonic state.

The neurotransmitter norepinephrine is similar in structure to dopamine and is a somewhat milder stimulant of the central nervous system. Amphetamines, similar in chemical structure to both norepinephrine and dopamine, are now believed to achieve their anorexient effects by inactivating reuptake transporter molecules that would normally bring dopamine and, perhaps, norepinephrine back from the synapse into the axon from which these neurotransmitters originated. Dexedrine is one of the "diet pills" of old and the prototype amphetamine.

Like the similar dopamine agonists, norepinephrine agonists, tend to be stimulating, so they should be used advisedly as anorexients.

Welbutrin, a combined norepinephrine and weak dopamine agonist, has the additional effect of enhancing female sexual response (though its sexual effect in men is neutral), so it can be useful in those women who encounter impaired sexual function as a side effect of certain SSRIs. It can, of course, be used in men, and its use in conjunction with an SSRI can potentate the anorexient qualities of both drugs as well as balance their side effects.

Phenylpropanolamine (PPA)

This mild stimulant, available in such preparations as Phenoxine and Dexatrim, is sold over-the-counter as timed-release or slow-acting preparations. PPA is also available by prescription in more concentrated form. PPA can be a valuable anorexient because of its rapid action. One can take the fast-release versions about half an hour before anticipating temptation and they will be finished working in a few hours.

In all likelihood, PPA, like amphetamine-related compounds, stimulates accumulation of norepinephrine and dopamine in synapses. It has some similar side effects which include insomnia, blood sugar and blood pressure elevation, rapid heart rate, sweating and agitation. When used in combination with another anorexient, L-tyrosine (an amino acid), the effectiveness of both are sometimes enhanced.

Centrally Acting Alpha-2 Agonists

Clonidine is a centrally acting alpha-2 agonist, a designation that refers to a particular type of receptor in the central nervous system. Alpha-2 agonists are actually marketed for the treatment of hypertension. They appear to enhance the affinity of the alpha-2 receptors for norepinephrine and possibly dopamine, and thereby as a side effect, can bring about more healthy appetite regulation. The alpha-2 agonists are quite effective in controlling high blood pressure and also, for perhaps one third of their users., are also quite effective as anorexients.

Amino Acids

Amino acids are the building blocks of proteins. There are a few specific amino acids from which the nervous system creates the neurotransmitters of interest.

5-hydroxytryptophan is an even closer precursor of serotonin than L-tryptophan. 5-hydroxytryptophan is the only anorexient amino acid that requires a prescription, and it can be purchased from pharmacies that employ a licensed compounding chemist.

L-glutamine is itself a neurotransmitter as well as a dopamine precursor and can be effective for some people in anticipation of temptation. It is not clear whether its anorexient effect is as a dopamine agonist or as a neurotransmitter or both. The latter seems possible because it's so fast-acting. It starts to work within half an hour, but should be used sparingly in order to avoid developing a tolerance.

L-tyrosine is a precursor of both norepinephrine and dopamine, but also potentiates serotonin. Tyrosine can be used in combination with Dexedrine or PPAs to make them more effective.

L-phenylalanine is, like tyrosine, a norepinephrine and dopamine precursor and can be used in conjunction with SSRIs to enhance their effect as anorexients.

Herbs

Prescription drugs and even over-the-counter cold preparations must typically go through rigorous testing over a period of several years in order to secure Food & Drug Administration (FDA) approval: lab testing, animal testing, and eventually clinical trials on humans. As a consequence of all this research, we usually know which neurotransmitters or receptors they affect, what kind of side effects they can have, and what the optimal dosages are. Herbal products are available over-the-counter as "dietary supplements" and can make no claims about their medicinal value.

Ma-huang is derived from the ephedra plant, and the substance that acts as an anorexient is ephedrine, which has been used as nose drops. Ephedrine is a mild stimulant and can constrict blood vessels, speed up the heart, and cause insomnia. Just as with the PPAs and the amphetamines, it should be used with caution.

For the purposes of clarity, only a few of the available and known anorexients have been specifically named herein. Those skilled in the art will appreciate that some are listed in the Physician's Desk Reference under the heading of "Antidepressants", and sub-headings "Selective Serotonin Reuptake Inhibitors" and "Miscellaneous". The reference also includes dosage information, for safe and effective dosage levels for each medication.

Rules & Guidelines For the Use of Anorexients

First, no single drug or anorexient agent works for everyone.

Second, for almost everyone, at least two anorexient agents and probably many agents or combinations exist that will control carbohydrate addiction.

Third, it appears that no anorexient agent keeps working indefinitely if used continuously. The development of a tolerance appears to be preventable if you establish a rotating regimen, use a particular agent for a period of time, for example a week, discontinue it and replace it with another for the next period of time. For the third period of time, you can return to the first agent without any loss of effectiveness. Occasionally, an individual may require three or four different periodic regimens to avoid the development of a tolerance.

A study completed more than a decade ago at the University of Rochester combined the serotonin agonist Pondimin with the amphetamine related compound phentermine (Ionamin) to evaluate the two drugs as an anorexient combination. The researchers used both drugs at minimal doses with the idea of limiting side effects. Indeed, side effects were limited, but the study over the course of four years was not very successful. Some patients did lose weight at first, but by the end of the trial, only a few had taken weight off and kept it off. The most important aspect of the study is that the vast majority of people develop a tolerance to the anorexient properties of these drugs if they take them long enough, without interruption (that is, without alternating with other medications). Again, this appears to be true of all anorexients.

If a given subject has been overweight for years and suddenly a particular product helps control the appetite, the perfectly natural reaction is to take it week after week. Do not. It does not work that way. Always alternate different medications at least week to week.

Fourth, if you are using a prescription drug from one category during week one; for example a serotonin agonist, try not to use the same category of medication during week two; use, perhaps, a norepinephrine-dopamine agonist. Drugs or agents from the same class can interact with the same receptors, producing a tolerance.

There are occasional exceptions to this rule, so it is not as rigid as the others. You might find, for example, a serotonin agonist effective during week 1 and a combination serotonin-norepinephrine-dopamine agonist effective for week 2. With anorexients, it is important to remember that research is continually evolving and I am learning of new anorexients at the rate of one or two every month, if we include herbal products.

Fifth, if a given anorexient agent is only partially effective in controlling carbohydrate craving, another agent, itself only partially effective, may be added during the same treatment period, to get 100% control.

Sixth, prescription drugs tend to have more side effects than mixtures of herbs. But any drug or even any herbal or amino acid preparation can have any side effect in a given individual; the side effects profile varies from anorexient to anorexient and person to person. Most, for the majority of individuals, do not have side effects.

Seventh, if a side effect is a concern, avoid it by either dropping the medication altogether or using it in conjunction with a preparation with the opposite side effect, or the opposite direct effect. There are, for example, many anorexients that can cause insomnia in some people. But these can be combined with other anorexients that might cause somnolence. The side effects of one will likely offset the side effects of the other.

Eighth, it is best to keep doses of prescription drugs and herbs to the lowest level possible because side effects are less likely at lower doses. Of course the likelihood of developing a tolerance is also increased at higher doses. Often the better strategy is to keep the dose as low as possible and combine it with another medication, also at a low dose. Furthermore, the lower the dose, the lower the cost.

Ninth, if the subject has a predisposition to a particular problem, such as constipation, insomnia, hypertension or panic disorder, it would be wise to start off with a preparation that carries the opposite side effect or direct effect. There are enough anorexients available that there is no reason whatsoever to increase problems.

Tenth, medications should be keyed to a patient's carbohydrate clock. If the subject tends to snack all day long, use a long-acting anorexient once or twice during the day. Alternately, use short-acting anorexients every few hours. If the craving only occurs at mealtime, then a rapid-acting product one to two hours before meals may suffice.

Eleventh, if an anorexient is going to work, its effect will be seen the first time you try it. If you are taking the appropriate dose, it should give complete efficacy. If you only get partial efficacy, then you probably need to step up the dose. Since I usually start at the lowest dose, sometimes my patients might not feel any change. We then try a higher dose. If after the higher dose you still felt nothing, then it would be time to go on to something else. There is no need to continue taking a preparation for days or weeks in the hope that it will eventually become effective. It usually will not. Prozac, for example, can require up to two weeks to attain its desired level of efficacy in those people who use it as an anti-depressant. However, for whatever reason, when you use it as an anorexient, it will most often begin to work at least partially with the first dose. The exceptions to this rule are rare.

Twelfth, very obese people will require higher doses of most anorexients. Using the PDR's maximum recommended dose will be less likely to cause side effects in such individuals but doses can be lowered as they approach ideal body weight.

Thirteenth, if weight loss reaches a plateau, in spite of adherence to our diet, the use of drugs like metformin (Glucophage), which lower insulin resistance, usually facilitates further weight reduction.

The manner and process of carrying out the method of the invention will be described further with reference to the following examples.

EXAMPLE 1

J. is not overweight and has no family history of obesity, but she is a Type 1, insulin-dependent diabetic in her forties who was unable to control her blood sugar because of her carbohydrate craving. As a result of her high blood sugars, she developed macular edema, a swelling of the central portion of the retina of the eye which can impair central vision and lead to permanent damage. Following an anorexient regimen that allows her to keep her blood sugar essentially normal, her retinologist reports that her macular edema is reversing. She has been diabetic only thirteen years, and macular edema was diagnosed about three years ago.

Her anorexient regimen is peculiar. On week one, 45 minutes before meals, three times a day, she takes one capsule of Citri-Max, which is hydroxycitric acid derived from the rind of the fruit of the garcinia cambulgia.

On week two, she takes the SSRI Luvox (fluvoxamine), a small dose, half of a 50 mg tablet on arising and half after lunch. The schedules of the two medications are different because Luvox works for about half a day whereas the Citri-Max only works for a few hours. This combination, arrived at through trial and error, totally controls her carbohydrate craving except if something tempting is placed in front of her.

EXAMPLE 2

P. S. was diagnosed with Type I diabetes about ten years ago, following the birth of her son. After going on insulin, she gained about a hundred pounds. (P. S. has a family history of obesity.) Initially, she complained of chronic flatulence and granuloma annulare, a skin condition not uncommon to poorly controlled diabetics. She also had a number of other problems related to her diabetes.

In a period of nine months, we have gotten her weight down from 222 pounds to 177, and have normalized her blood sugars as weight loss continues. She no longer complains of flatulence, and her granuloma annulare has cleared. For about three months we experimented with a number of regimens before we came up with something that works consistently.

Her big eating problem had occurred during and after dinner. Her regimen on week one consists of 5 mg of Dexedrine one and one-half hours before dinner. In week two, it is 20 mg of Pondimin, also one and a one-half hours before dinner. It is interesting that such a simple regimen works so well. The only time she finds herself overeating is when she forgets her pills. Her low dose of Dexedrine does not keep her up at night. It has mostly worn off by then, but it is such a low dose that it probably would not keep her up even if she took it at bedtime.

EXAMPLE 3

J., a compulsive gambler in his fifties, came to me for treatment of his extreme obesity in July of 1995. He has a family history of obesity and diabetes. He constantly craved bread, pasta, and potatoes. We did some initial blood work on him and discovered that he had a mild form of Type II diabetes, based upon a hemoglobin $A_{1C}$ of 6.0, which for our lab corresponds to an average blood sugar of 140 mg/dl. We started treating J. with a low carbohydrate diet a week after his initial visit. He is 5'9-½" tall and his weight at that time was 289. In the course of about a month, he had lost 23 pounds.

When I examined him, he showed a number of diabetic complications, suggesting that he has had a mild form of the disease for many years. ("Mild" in the case of diabetes, is an entirely relative term. Although his disease had not killed him, some of the complications I found in my examination could, over the years, cripple, blind, or eventually kill him).

In J.'s case, we are simultaneously addressing his obesity, his diabetes, and his compulsive gambling. Currently, his medical regimen includes daily doses of Luvox week in and week out. The Luvox as an anorexient will wear off over the course of a few weeks or months, but it does seem to have a lasting effect on his compulsive gambling, and he reports that since being on it he has lost much of the desire to gamble.

His eating behavior is being controlled with two different herbal preparations. Since his cravings occur all day long, he has to take his anorexients frequently. During week one, he takes Citri-Life, which is a mixture that includes the herbal extract contained in Citri-Max and about a dozen other herbs. He takes this preparation every three hours. During week two, he takes a product called Homeopathic Weight Loss, a capsule containing a mixture of about fifteen different herbs. He takes one capsule every four hours. This combination works well for him, and his blood sugar levels are now always normal, in the non-diabetic range.

EXAMPLE 4

B. is a fifty year-old non-diabetic woman who carried 201-½ lbs on a 5'1" frame. In just about seven months she had come down to 142-½ lbs. Although she is not diabetic and has no family history of diabetes, she does have a family history of obesity. Her hemoglobin $A_{1C}$ was 5.2, which corresponds to an average blood sugar of about 108 mg/dl, which is a little more than the average blood sugar of the general population and therefore made me somewhat suspicious of potential diabetes. Because of her short frame, you would probably classify her as morbidly obese when I first saw her. She now looks almost normal, and like the other patients discussed here, is still losing weight.

The anorexient regimen that worked well for her was as follows: During week one, she used Appe-Tight, which is a mixture of about 15 herbs, plus L-phenylalanine and lecithin. She took two pills of Appe-Tight, on arising, two with lunch, and two in the late afternoon. Most of her snacking occurred when she came home from work at about 4:00 P.M. and would continue until dinner-time, which would be at about 8:00 P.M. Now the snacking is gone. Her week two regimen was Extra Thin Formula 59, which contains eleven different herbs. She took two pills on the same schedule as the Appe-Tight.

By the time we got her weight down to about 175 lbs., she stopped taking the anorexients because she found she no longer had the carbohydrate craving. Since that time, she reported one episode of craving, for which she took one of the Formula 59 tablets. It started working in about an hour and she felt comfortable thereafter.

It is interesting that over the course of this short time frame, her serum fibrinogen, which is an important measure of cardiac risk, came down from 396, a high normal value, to 312. Her homocysteine, another cardiac risk factor, came down from a high 18 to 9, which is roughly in the mid-normal range. It is difficult to determine whether it was the weight loss that brought about these positive changes or the low carbohydrate diet, but we often see such improvements in patients who reduce their carbohydrate consumption.

EXAMPLE 5

M. R. is in his fifties. He has no family history of diabetes, but his mother was obese. His initial hemoglobin $A_{1C}$ was 5.5, which corresponds to an average blood sugar level of about 120 mg/dl. Some might not consider that value high enough to diagnose Mike as diabetic, but I diagnosed him as having a mild form of Type II diabetes, which was confirmed by his blood sugar self-monitoring records. His weight came down to 209-½ lbs., more than a fifty pound drop, in nine months. We used anorexients all along the way.

M. R.'s eating problem was all day, but concentrated before and after dinner. On week one, he takes Tenuate Dospan, a long-acting amphetamine like medication, half a 75 mg tablet at 10:00 A.M. He supplements this with seawrack (one of the few herbs I will recommend for use by itself instead of in a mixture), two tablets one and one-half hours before dinner and two after dinner. The long-acting Tenuate lasts him about twelve hours, and the seawrack at night takes care of his evening cravings.

On week two, he takes 50 mg of Luvox on arising, and 50 mg after lunch. Since each dose of Luvox works for about twelve hours, these two doses control both his daytime and evening cravings. He finds this regimen 100% effective.

Interestingly, he went away for three weeks, did not take his pills with him, and gained seven pounds. We have also been treating him with metformin (an oral hypoglycemic agent, or OHA), principally for control of his weight, but it has also helped his blood sugars. After about three months on our regimen, his hemoglobin $A_{1C}$ dropped from 5.5 to 5.2, and now it is well within the non-diabetic range. We have yet to get him to exercise, but he has finally made an appointment for a cardiac stress test, which for sedentary adults over the age of forty, should precede a strenuous exercise routine.

EXAMPLE 6

R. is in her forties. She had Type II diabetes on both sides of her family, but she came to our Diabetes Center with a normal hemoglobin $A_{1C}$ of 4.7, one of the few people I have treated for obesity who started with a normal $A_{1C}$. Interestingly, her daughter, whom she brought to see me and is only slightly obese, has a slightly elevated $A_{1C}$.

We started working with R. in early August 1994. When she first came in, carrying 184 lbs on a five-foot five-inch frame, she was certainly not physically attractive. Less than a year later, she had lost close to 55 lbs, and weighed 130. She had transformed from a big, matronly looking woman with triple chins into a very chic, sexy-looking lady. It simply had not been apparent how pretty she might be when she had three chins.

Although she looks fine at her current weight, she wants to take off a few more pounds, which is not inappropriate as long as we get her to level off at 115–125 lbs. At her last visit, she was so pleased with her accomplishment, she stripped down to her bathing suit and impressed the whole office.

R.'s history is an unusual one because four months after she started on her anorexient regimen, her weight leveled off, and by putting her on metformin, even though her blood sugars were within the normal range, we were able to achieve further weight loss. She takes two 500 mg metformin tablets on arising, one before lunch, one before dinner, and one at bedtime. We had her measure her blood sugar levels as she would if she were a diabetic to make sure her blood glucose did not go too low. We found, though, that when we were concentrating the metformin at bedtime, it was going too low in the morning. Her current regimen keeps it normal around the clock.

During week one, her anorexient regimen is a single Catapres, (Clonidine, an anti-hypertensive agent), size 2 skin patch. Her eating problem had been all day long, at least while she was awake, and so the 24-hour-a-day patch is appropriate. During week two, she takes 5 mg of Dexedrine at 11:00 A.M., 5 mg at 2:30 P.M., and 10 mg at 5:00 P.M. This is a fast-acting dextroamphetamine, not a timed-release product. We are giving her this because I find that the fast-acting versions work more effectively than the timed-release. By giving her the dextroamphetamine on alternate weeks, she is never on it long enough for me to worry about her becoming chemically or psychologically dependent. Unlike B., who found her anorexients unneeded after a period of time, the chances are that R. may have to stick with the skin patch one week and the Dexedrine the next week for the rest of her life. At this point, however, we cannot know for sure. It is likely that she will not have to continue the metformin for the rest of her life, because as a slim person, she is probably no longer insulin-resistant. Insulin resistance is reduced by metformin. This is the mechanism by which it reduces blood sugar in type II diabetics. Since insulin is a major fat-building hormone, individuals with insulin resistance will make more insulin and therefore more fat.

What is claimed is:

1. A method for alleviating carbohydrate addiction in a human suffering from said addiction, which comprises;
    a. administering to a human suffering from carbohydrate addiction a first anorexient or combination of anorexients in amounts sufficient to relieve the addiction for a period of time insufficient to develop tolerance to the administration; and
    b. then replacing said anorexient or combination of anorexients with an appropriate amount of a different anorexient or combination of anorexients; and
    c. repeating steps a. and b. over and over; whereby the addiction is alleviated, for as long as the anorexient regimen continues.

2. A method of claim 1 wherein the period of time is about 1 week.

3. A method of claim 1 wherein the period of time is about 1 week to about 3 months.

4. A method of claim 1 wherein the period of time is from about 1 day to about 6 months.

5. A method of claim 1 wherein at least one of anorexients is a serotonin agonist.

6. A method of claim 1 wherein at least one of the anorexients is a selective serotonin reuptake inhibitor.

7. A method of claim 1 wherein at least one of the anorexients is a dopamine and/or norepinephrine agonist.

8. A method of claim 1 wherein at least one of the anorexients contains phenylpropanolamine.

9. A method of claim 1 wherein at least one of the anorexients is is a centrally acting alpha-2 agonist.

10. A method of claim 1 wherein at least one of the anorexients is an amino acid.

11. A method of claim 1 wherein at least one of the anorexients is a natural herb or mixture of natural herbs.

12. The method of claim 1 which further comprises administering to the human, an effective amount of metformin to lower insulin resistance.

13. A method of alleviating carbohydrate addiction in a human suffering from said addiction, which comprises;
    a. administering to a human suffering from carbohydrate addiction a first anorexient or combination of anorexients in amounts sufficient to relieve the addiction for a period of time; and
    b. changing the anorexient or combination of anorexients periodically thereafter, to avoid building a tolerance for the anorexient or combination of anorexients; and repeating the steps a. and b. in sequence a plurality of times.

14. The method of claim 13 wherein changes are made about 1 week to about 6 months after the initial administration.

15. A method of claim 13 wherein the period of time is about 1 week.

16. A method of claim 13 wherein the period of time is about 1 week to about 3 months.

17. A method of claim 13 wherein the period of time is from about 1 day to about 6 months.

18. A method of claim 13 wherein at least one of anorexients is a serotonin agonist.

19. A method of claim 13 wherein at least one of the anorexients is a selective serotonin reuptake inhibitor.

20. A method of claim 13 wherein at least one of the anorexients is a dopamine and/or norepinephrine agonist.

21. A method of claim 13 wherein at least one of the anorexients contains phenylpropanolamine.

22. A method of claim 13 wherein at least one of the anorexients is a centrally acting alpha-2 agonist.

23. A method of claim 13 wherein at least one of the anorexients is an amino acid.

24. A method of claim 13 wherein at least one of the anorexients is a natural herb or mixture of natural herbs.

25. The method of claim 13 which further comprises administering to the human, an effective amount of metformin to lower insulin resistance.

26. A method of alleviating carbohydrate addiction in a human suffering from said addiction, which comprises;
    a. administering to a human suffering from carbohydrate addiction a first anorexient or combination of anorexients in amounts sufficient to relieve the addiction for a period of time; and
    b. changing the anorexient or combination of anorexients periodically thereafter to a second anorexient or combination of anorexients in amounts sufficient to relieve the addiction for a second period of time;
    c. changing the second anorexient or combination of anorexients to a third anorexient or combination of anorexients in amounts sufficient to relieve the addiction for a third period of time.

27. The method of claim 26 which further comprises changing the third anorexient or combination of anorexients to a fourth anorexient combination of anorexients sufficient to relieve the addiction for a fourth period of time.

* * * * *